United States Patent
Hamad-Schifferli et al.

(10) Patent No.: US 9,545,383 B2
(45) Date of Patent: Jan. 17, 2017

(54) BLOOD CLOTTING CONTROL

(71) Applicant: Massachusetts Institute of Technology, Cambridge, MA (US)

(72) Inventors: Kimberly Hamad-Schifferli, Somerville, MA (US); Salmaan H. Baxamusa, Livermore, CA (US); Helena de Puig Guixe, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/675,248

(22) Filed: Mar. 31, 2015

(65) Prior Publication Data

US 2015/0272899 A1    Oct. 1, 2015

Related U.S. Application Data

(60) Provisional application No. 61/973,290, filed on Apr. 1, 2014.

(51) Int. Cl.

| | | |
|---|---|---|
| *A61N 1/30* | (2006.01) | |
| *A61K 9/51* | (2006.01) | |
| *A61K 41/00* | (2006.01) | |
| *A61K 47/48* | (2006.01) | |
| *A61K 31/713* | (2006.01) | |
| *A61K 31/00* | (2006.01) | |
| *A61N 5/06* | (2006.01) | |

(52) U.S. Cl.
CPC ............. *A61K 9/5115* (2013.01); *A61K 31/00* (2013.01); *A61K 31/713* (2013.01); *A61K 41/0028* (2013.01); *A61K 47/48884* (2013.01); *A61N 5/062* (2013.01)

(58) Field of Classification Search
None
See application file for complete search history.

(56) References Cited

U.S. PATENT DOCUMENTS

| | | | |
|---|---|---|---|
| 6,685,730 B2 | 2/2004 | West et al. | |
| 7,488,792 B2 | 2/2009 | Ruoslahti et al. | |
| 7,723,315 B2 | 5/2010 | Rusconi | |
| 8,063,018 B2 | 11/2011 | Ni et al. | |
| 8,319,002 B2 | 11/2012 | Daniels et al. | |
| 8,455,439 B2 | 6/2013 | Lu et al. | |
| 2005/0176940 A1* | 8/2005 | King | A61K 31/7088 536/23.1 |
| 2008/0305101 A1 | 12/2008 | Ruoslahti et al. | |
| 2010/0040554 A1* | 2/2010 | Li | A61K 49/0054 424/9.6 |

FOREIGN PATENT DOCUMENTS

| | | |
|---|---|---|
| WO | WO 2008/107489 A1 | 9/2008 |
| WO | WO 2009/027507 A2 | 3/2009 |
| WO | WO 2009/052301 A1 | 4/2009 |
| WO | WO 2010/002949 A2 | 1/2010 |
| WO | WO 2010/117729 A1 | 10/2010 |
| WO | WO 2011/008885 A1 | 1/2011 |
| WO | WO 2011/075725 A1 | 6/2011 |
| WO | WO 2011/084700 A1 | 7/2011 |

OTHER PUBLICATIONS

Ahmad et al., Probing the limits of aptamer affinity with a microfluidic SELEX platform. PLoS One. 2011;6(11):e27051. doi: 10.1371/journal.pone.0027051. Epub Nov. 14, 2011.
Blossom et al., Outbreak of adverse reactions associated with contaminated heparin. N Engl J Med. Dec. 18, 2008;359(25):2674-84. doi: 10.1056/NEJMoa0806450. Epub Dec. 3, 2008. Erratum in: N Engl J Med. Mar. 18, 2010;362(11):1056.
Bock et al., Selection of single-stranded DNA molecules that bind and inhibit human thrombin. Nature. Feb. 6, 1992;355(6360):564-6.
De Puig et al., Quantifying the nanomachinery of the nanoparticle-biomolecule interface. Small. Sep. 5, 2011;7(17):2477-84.
De Puig et al., Selective Light-Triggered Release of DNA from Gold Nanorods Switches Blood Clotting On and Off. PLOS ONE. Jul. 24, 2013. 8(7): e68511: 1-6. DOI: 10.1371/journal.pone.0068511.
Guerrini et al., Oversulfated chondroitin sulfate is a contaminant in heparin associated with adverse clinical events. Nat Biotechnol. Jun. 2008;26(6):669-75. doi: 10.1038/nbt1407. Epub Apr. 23, 2008.
Hamad-Schifferli, Engineering the Nanoparticle-Biology Interface. MIT: Mechanical Engineering. Apr. 2013. 1-23.
Heckel et al., An Anticoagulant with Light-Triggered Antidote Activity. Angewandte Chemie International Edition. Oct. 13, 2006. 45(40): 6748-50. DOI: 10.1002/anie.200602346.
Huang et al. Plasmonic photothermal therapy (PPTT) using gold nanoparticles. Lasers Med Sci. Jul. 2008;23(3):217-28. Epub Aug 3, 2007. Review. DOI: 10.1007/s10103-007-0470-x.
Huschka et al., Light-induced release of DNA from gold nanoparticles: nanoshells and nanorods. J Am Chem Soc. Aug. 10, 2011;133(31):12247-55. doi: 10.1021/ja204578e. Epub Jul. 20, 2011.
Joachimi et al., A New Anticoagulant-Antidote Pair: Control of Thrombin Activity by Aptamers and Porphyrins. J. Am. Chem. Soc. 2007. 129 (11): 3036-7. DOI: 10.1021/ja0677822.
Kaatz et al., Guidance on the emergent reversal of oral thrombin and factor Xa inhibitors. Am J Hematol. May 2012;87 Suppl 1:S141-5. doi: 10.1002/ajh.23202. Epub Apr. 4, 2012. Review. Erratum in: Am J Hematol. Jul. 2012;87(7):748.
Kah et al., Exploiting the protein corona around gold nanorods for loading and triggered release. ACS Nano. Aug. 28, 2012;6(8):6730-40. doi: 10.1021/nn301389c. Epub Jul. 26, 2012.
Kim et al., Using photons to manipulate enzyme inhibition by an azobenzene-modified nucleic acid probe. Proc Natl Acad Sci U S A. Apr. 21, 2009;106(16):6489-94. doi: 10.1073/pnas.0812402106. Epub Apr. 9, 2009.

(Continued)

Primary Examiner — Marcela M Cordero Garcia
(74) Attorney, Agent, or Firm — Wolf, Greenfield & Sacks, P.C.

(57) ABSTRACT

The disclosure is directed to enabling reversible, on-demand remote control of blood clotting and clot dissolution. In one embodiment, a laser at one wavelength triggers release of a DNA thrombin inhibitor from one nanorod, which acts as an anticoagulant to stop blood clotting. Another wavelength triggers release of a specific antidote, which reverses the effect of the thrombin inhibitor, restoring blood clotting.

24 Claims, 9 Drawing Sheets

(56) References Cited

OTHER PUBLICATIONS

Kishimoto et al., Contaminated heparin associated with adverse clinical events and activation of the contact system. N Engl J Med. Jun. 5, 2008;358(23):2457-67. doi: 10.1056/NEJMoa0803200. Epub Apr. 23, 2008. Erratum in: N Engl J Med. Mar. 18, 2010;362(11):1056.

Lefkovits et al., Direct thrombin inhibitors in cardiovascular medicine. Circulation. Sep. 1994;90(3):1522-36. Review.

Li et al., Electrochemical impedance spectroscopy for study of aptamer-thrombin interfacial. Biosensors and Bioelectronics. Jun. 15, 2008. 23(11): 1624-30. doi:10.1016/j.bios.2008.01.029.

Link et al. Laser-Induced Shape Changes of Colloidal Gold Nanorods Using Femtosecond and Nanosecond Laser Pulses. J Phys Chem B. 2000; 104(26): 6152-63. DOI: 10.1021/jp000679t.

Link et al., Shape and size dependence of radiative, non-radiative and photothermal properties of gold nanocrystals. International Rev Phys Chem. 2000. 19(3): 409-53. DOI:10.1080/01442350050034180.

Müller et al., Anticoagulant characteristics of HD1-22, a bivalent aptamer that specifically inhibits thrombin and prothrombinase. J Thromb Haemost. Dec. 2008;6(12):2105-12. doi:10.1111/j.1538-7836.2008.03162.x. Epub Sep. 27, 2008.

Padmanabhan et al. The structure of alpha-thrombin inhibited by a 15-mer single-stranded DNA aptamer. J Biol Chem. Aug. 25, 1993;268(24):17651-4.

Pagano et al., Stability and binding properties of a modified thrombin binding aptamer. Biophys J. Jan. 15, 2008;94(2):562-9. Epub Sep. 21, 2007.

Rusconi et al., Antidote-mediated control of an anticoagulant aptamer in vivo. Nat Biotechnol. Nov. 2004;22(11):1423-8. Epub Oct. 17, 2004.

Sau et al., Seeded high yield synthesis of short Au nanorods in aqueous solution. Langmuir. Jul. 20, 2004;20(15):6414-20.

Schwienhorst, Direct thrombin inhibitors—a survey of recent developments. Cell Mol Life Sci. Dec. 2006;63(23):2773-91. Review.

Shepherd et al., Adverse drug reaction deaths reported in United States vital statistics, 1999-2006. Ann Pharmacother. Feb. 2012;46(2):169-75. doi: 10.1345/aph.1P592. Epub Jan. 17, 2012.

Tasset et al., Oligonucleotide inhibitors of human thrombin that bind distinct epitopes. J Mol Biol. Oct. 10, 1997;272(5):688-98.

Wijaya et al., Ligand Customization and DNA Functionalization of Gold Nanorods via Round-Trip Phase Transfer Ligand Exchange. Langmuir, 2008. 24 (18): 9966-9.

Wijaya et al., Selective release of multiple DNA oligonucleotides from gold nanorods. ACS Nano. Jan. 27, 2009;3(1):80-6. doi: 10.1021/nn800702n.

Wysowski et al., Bleeding complications with warfarin use: a prevalent adverse effect resulting in regulatory action. Arch Intern Med. Jul. 9, 2007;167(13):1414-9.

\* cited by examiner

SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 1
ggttggtgtg gttgg                                                   15

<210> SEQ ID NO 2
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 2
aaccaacaca accaa                                                   15

BLOOD CLOTTING CONTROL

CROSS-REFERENCE TO RELATED APPLICATIONS

This application claims the benefit under 35 U.S.C. §119 (e) of U.S. provisional application Ser. No. 61/973,290, filed Apr. 1, 2014, the disclosure of which is incorporated by reference in its entirety.

GOVERNMENT FUNDING

This invention was made with government support under Grant No. DMR-0906838 awarded by the National Science Foundation. The government has certain rights in the invention.

FIELD

Disclosed embodiments are related to blood clotting control.

BACKGROUND

In wound healing and surgery, blood clotting must be controlled for patient safety. Blood clotting is triggered by an enzymatic cascade that ultimately activates the protein thrombin, which cleaves fibrinogen to form a clot. Manipulation of blood clotting is achieved predominantly by administering anticoagulants such as heparin, warfarin (coumarin), and others which inhibit blood clotting. However, these anticoagulants suffer many limitations, causing them to rank as the leading cause of death in adverse drug reactions in therapeutic use in the US. These anticoagulants can only inhibit coagulation, so their ability to control clotting is inherently one-sided. Furthermore, heparin, the most prevalently used anticoagulant, is a polydisperse polymer that acts nonspecifically, inhibiting not one but several species in the clotting cascade. Heparin is obtained from livestock (pig) intestines, where risk of contamination is significant and can be fatal. More importantly, these anticoagulants have no specific antidote, and reversing their effect is predominantly achieved by clearance, which can vary greatly among people. Current recommendations include use of activated charcoal to non-specifically absorb the drug.

SUMMARY

In one embodiment, a clotting inhibitor and a specific antidote with spatial and temporal control is used to control clotting. For example, a method for reversibly controlling blood coagulation may use gold nanorods and light. A laser at one wavelength triggers release of a DNA thrombin inhibitor from one nanorod, which acts as an anticoagulant to stop blood clotting. Excitation at another wavelength triggers release of a specific antidote, which reverses the effect of the thrombin inhibitor, restoring blood clotting. This technology enables on-demand, reversible, remote control of blood clotting.

In another embodiment, on demand, external control of blood clotting can be applied to first start and then stop blood clotting, allowing rapid cessation of bleeding.

In yet another embodiment, a composition includes a nanoparticle with a first excitation wavelength and a therapeutic agent selected from one of an antithrombotic agent and an antihemorrhagic agent attached to the nanoparticle. Excitation of the nanoparticle with a first excitation wavelength releases the therapeutic agent.

In another embodiment, a method for dissolving a clot includes: administering a first nanoparticle with a first excitation wavelength, wherein the first nanoparticle includes an antithrombotic agent attached to the first nanoparticle; administering a second nanoparticle with a second excitation wavelength different from the first excitation wavelength, wherein the second nanoparticle includes an antihemorrhagic agent attached to the second nanoparticle; exciting the first nanoparticle with the first excitation wavelength to release the antithrombotic agent; and exciting the second nanoparticle with the second excitation wavelength to release the antihemorrhagic agent.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
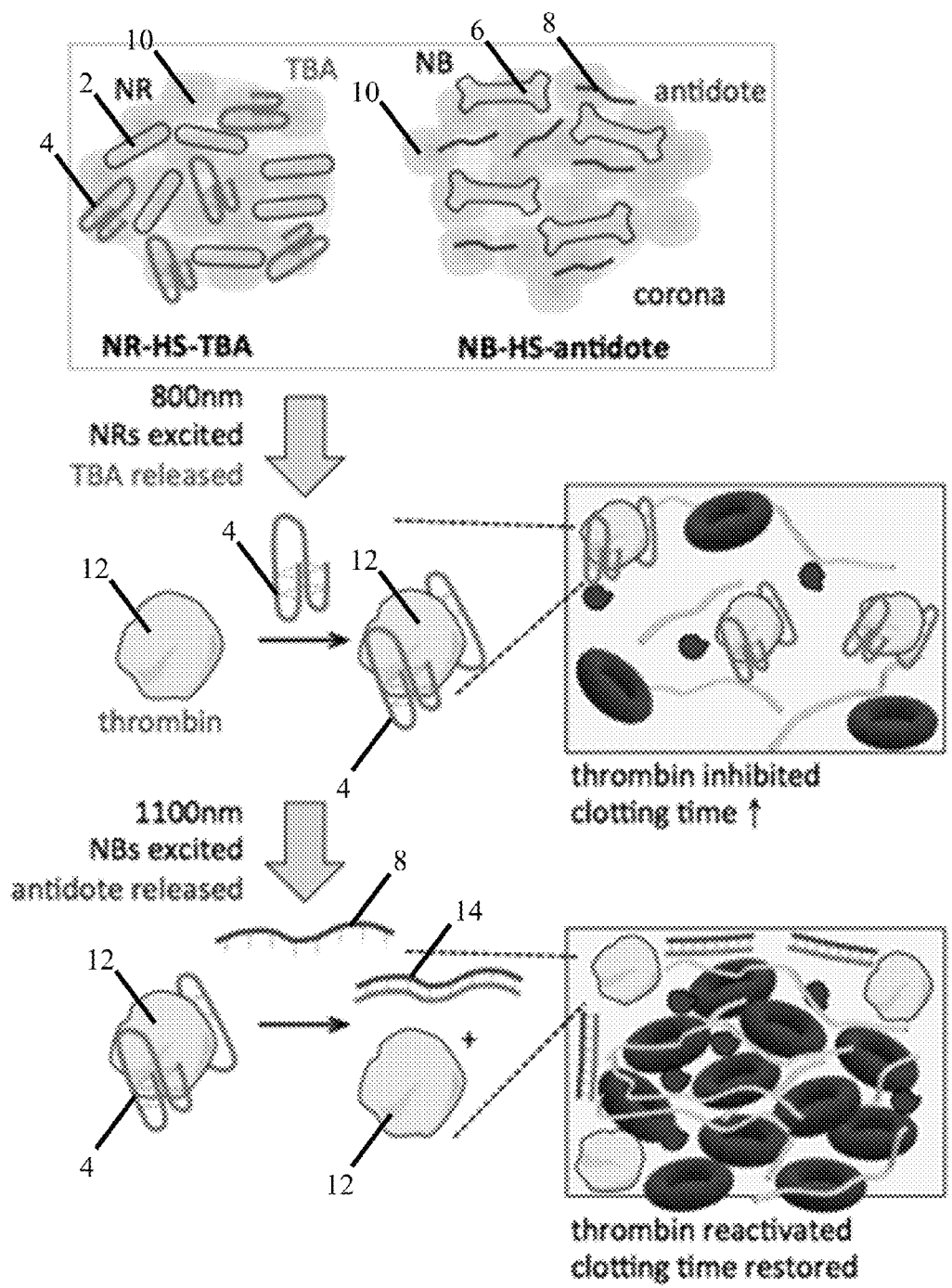
FIG. 1 is a schematic representation of the triggered release of a thrombin binding aptamer (TBA) and its antidote.

The inventors have recognized that current approaches to control clotting are sluggish. To reverse the effects of anticoagulants, the predominant method is to simply wait for clearance, which can add days onto inpatient times in the hospital both before and after surgery and is a major expense. In addition, clearance times can vary from patient to patient, so periodic monitoring is required. Because specific antidotes for existing anticoagulants are not known, methods include administration of fresh frozen plasma to induce clotting, but this is not rapid nor can be implemented in surgery as it is difficult to dose. Current state of the art recommendations to reverse the effects of anticoagulants include administration of activated charcoal. While activated charcoal can be used successfully, it does not work specifically.

In view of the above, the inventors have recognized a need for a technology that enables reversible, on-demand remote control of blood clotting. For example, control of blood coagulation by light may be achieved by using gold nanoparticles.

In one embodiment, an inhibitor and a specific antidote with spatial and temporal control may be used to control clotting. For example, in a specific embodiment, a method for reversibly controlling blood coagulation uses gold nanorods and light. A laser at one wavelength triggers release of a DNA thrombin inhibitor from one nanorod, which acts as an anticoagulant to stop blood clotting. Excitation by a laser at another wavelength triggers release of a specific antidote, which reverses the effect of the thrombin inhibitor, restoring blood clotting. This technology enables on-demand, reversible, remote control of blood clotting.

The methods and materials described herein may help to improve surgery. For example, the disclosed methods and materials may be used to temporarily suspending blood coagulation for transplants and other surgeries. This may be especially useful in microsurgeries where it is necessary to connect small diameter vessels (roughly a few millimeters in diameter) which are highly susceptible to being clogged by clot formation.

In addition to the above noted applications, on demand, external control of blood clotting can be applied to first start and then stop blood clotting, which can be used for rapid halting of bleeding.

Depending on the embodiment, blood coagulation may be controlled by a thrombin binding aptamer (TBA), a nucleic acid strand (typically DNA or RNA)<40 nucleotides long that specifically inhibits thrombin, by binding to it. Several thrombin inhibiting aptamers have been discovered using systematic evolution of ligands by exponential enrichment (SELEX). For example, TBA with the sequence 5'GGTTG-GTGTGGTTGG (SEQ ID NO: 1) may be used.

In some embodiments, complementary DNA may act as an antidote to TBA by base-pairing with it as further described below with regards to FIG. 1. For example, addition of the DNA complement (sequence 5'AAC-CAACACAACCAA (SEQ ID NO: 2)) at ratios from 0:1 to 2:1 antidote:TBA may result in clotting time returning to normal as described further below in regards to FIGS. 3A and 3B.

In one embodiment, DNA aptamers are loaded onto nanoparticles by direct adsorption, covalent attachment, or by formation of protein coronas around the nanoparticles. Without wishing to be bound by theory, protein coronas may have several advantages as they can hold a large amount of payload and minimize damage to the payload upon laser irradiation. For example, nanorods loaded with DNA can be isolated from free DNA and other species by centrifugation. TBA may then be loaded onto short nanorods in one separate solution, and a DNA antidote may be loaded onto long nanorods in another solution.

Without wishing to be bound by theory, control of blood coagulation by light may be achieved by using gold nanoparticles, which absorb strongly due to their surface plasmon resonance (SPR). If the nanoparticle is rod-shaped, then it has both a transverse and a longitudinal SPR, the latter of which is strongly shape dependent and which may coincide with the wavelength range where tissue is transparent. The wavelength of the SPR maximum varies with nanorod shape and size, so two nanorods can be chosen such that their SPRs do not overlap. Laser excitation at the SPR heats the nanoparticle, triggering release of a payload on the nanoparticle. Gold nanorods may be synthesized using literature methods to have two different sizes and thus minimally overlapping SPRs. Thus in one embodiment, a laser at one wavelength may be used to trigger the release of a DNA thrombin inhibitor from one nanorod, which acts as an anticoagulant to stop blood clotting, and another wavelength may be used to trigger release of a specific antidote to reverse the effect of the thrombin inhibitor.

Turning now to the figures, several embodiments are described in further detail. However, it should be understood that the current disclosure is not limited to only the embodiments described herein. Instead, the disclosure should be interpreted generally as applying to any appropriate combination of components, materials, and features described herein with regards to the various embodiments.

FIG. 1 depicts gold nanorods 2 and 6 for reversible control of blood clotting by light. The nanorods due to their size and material dependent properties, can be excited by lasers in a mutually exclusive manner to enable selective release of a thrombin inhibiting aptamer and its antidote. For example, as depicted in the figure, laser excitation at one wavelength is used to selectively excite one nanorod 2, triggering release of the thrombin inhibitor 4 for stopping blood clotting. The other wavelength may then excite the other nanorod, 6 releasing the antidote 8, which binds to the thrombin binding aptamer, restoring thrombin activity and thus blood clotting. In a specific embodiment, the short nanorods 2 are loaded with TBA 4 and the long bone-shaped nanorods 6 are loaded with antidote 8. In one embodiment, 800 nm laser irradiation melts the nanorods 2 triggering release of TBA which inhibits thrombin 12 and causes blood coagulation times to increase. To reverse the effect, 1100 nm laser irradiation may be used to melt the nanobones 6, triggering release of the DNA antidote from the corona 10. The antidote forms a double-stranded hybrid 14 with TBA, thus restoring thrombin activity and blood coagulation. In view of the above, the triggered release of TBA and its antidote can be used to reversibly switch blood coagulation.

As noted above, nanoparticles and light can also be used to start and stop clotting. In one such an embodiment, a coagulant, such as thrombin, may be loaded on a nanoparticle. A corresponding nanoparticle may be loaded with an anticoagulant, such as a thrombin inhibitor. Similar to the above, first and second excitation wavelengths may then be used to selectively release the coagulant and anticoagulant from the nanoparticles to selectively start and stop clotting.

Similar to the above, nanoparticles and light may also be used to control the dissolution of clots. Specifically, an antithrombotic agent capable of aiding the dissolution of a clot may be loaded onto a first nanoparticle and an antihemorrhagic agent capable of stopping clot dissolution may be loaded onto a second nanoparticle. Release of these agents may then be controlled as previously described using different excitation wavelengths.

It should be understood that any appropriate compound can be used to dissolve a clot. As noted above, in some embodiments an antithrombotic agent may be used including one or more of: an anticoagulant such as Coumarin derivatives (including Warfarin Sodium), Direct thrombin inhibitors (including Agatroban, Bivalirudin Dabigatran Etexilate Mesylate, Desirudin, and Lepirudin), Direct factor Xa inhibitors (including Apixaban, Fondaparinux Sodium, and Rivaroxaban), Heparins (including Dalteparin Sodium, Enoxaparin Sodium, Heparin Sodium), and other anticoagulants (including Antithrombin III (Human), Antithrombin alpha, Protein C (human)); Platelet reducing agents such as Anagrelide hydrochloride; Platelet aggregation inhibitors such as Abciximab, Cilostazol, Clopidogrel Hydrochloride, Ticaegrelor, Ticlopiridine Hydrochloride, Tirofiban, Aspirin, Dipyridamole, and Sulfinpyrazone; and Thrombolytic agents such as Alteplase (t-PA), Reteplase (t-PA), Tenecteplase (t-PA), kallikrein, and urokinase (u-PA) to note a few.

In addition to the above, it should be understood that any appropriate compound can be used to stop clot dissolution. As noted above, in some embodiments an Antihemorrhagic agent may be used including one or more of: an Antiheparin agent such as Protamine Sulphate; a Hemostatic agent including Aminocaproic Acid, Antihemophillic Factor (Human), Antihemophillic Factor (Porcine), Antihemophillic Factor (Recombinant), Anti-inhibitor Coagulant Complex, Aprotinin, Factor VIIa (Recombinant), Factor IX (Human), Factor IX Complex (Human), Factor IX (Recombinant), Factor XIII (Human), Fibrinogen (Human), Prothrombin Complex Concentrate (Human), Thrombin alfa, Thrombin (Bovine), Thrombin (Human), Desmopressin (Hemophilia A and von Willebrand Disease); and a plasmin inhibitor such as plasminogen activator inhibitor (PAI-1) and alpha2-antiplasmin to note a few.

In one exemplary embodiment using the materials and agents noted above, clot dissolution may be initiated by exciting a first type of nanoparticle loaded with a plasmin activator such as tissue plasminogen activator (tPA), kallikrein, and urokinase (u-PA). Clotting may then be stopped by exciting a second type of nanoparticle loaded with a plasmin inhibitor such as aprotinin, PAI-1, and alpha2-antiplasmin.

Figure 2A:
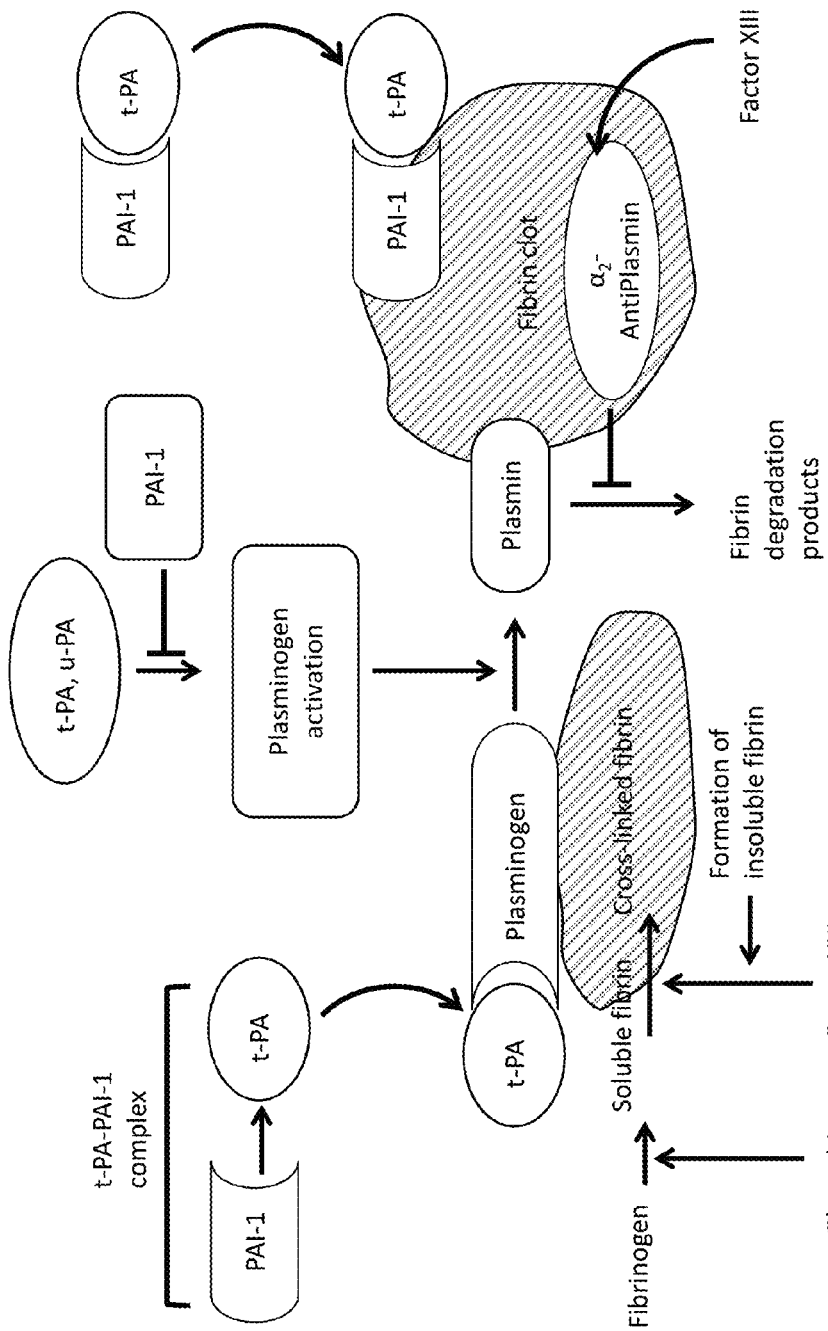
FIG. 2A is a schematic representation of the protein cascade for thrombolysis.

FIG. 2A presents a schematic representation of the processes governing the dissolution and formation of a clot. As illustrated in the figure, the protein responsible for clot dissolution is plasmin, which breaks down the clot into fibrin degradation products. Plasmin is normally in an inactive form as plasminogen. Plasminogen activators, such as urokinase plasminogen activator (u-PA) and tissue plasminogen activator (t-PA), circulate in plasma as a reversible complex with PAI-1. When a fibrin clot is formed, plasminogen and t-PA or u-PA bind to the clot and form plasmin which results in lysis of the cross linked fibrin to fibrin degradation products. PAI-1 may also bind to fibrin and when bound, can irreversibly inhibit plasminogen activators and is thereby termed a "suicide inhibitor."

Figure 2B:
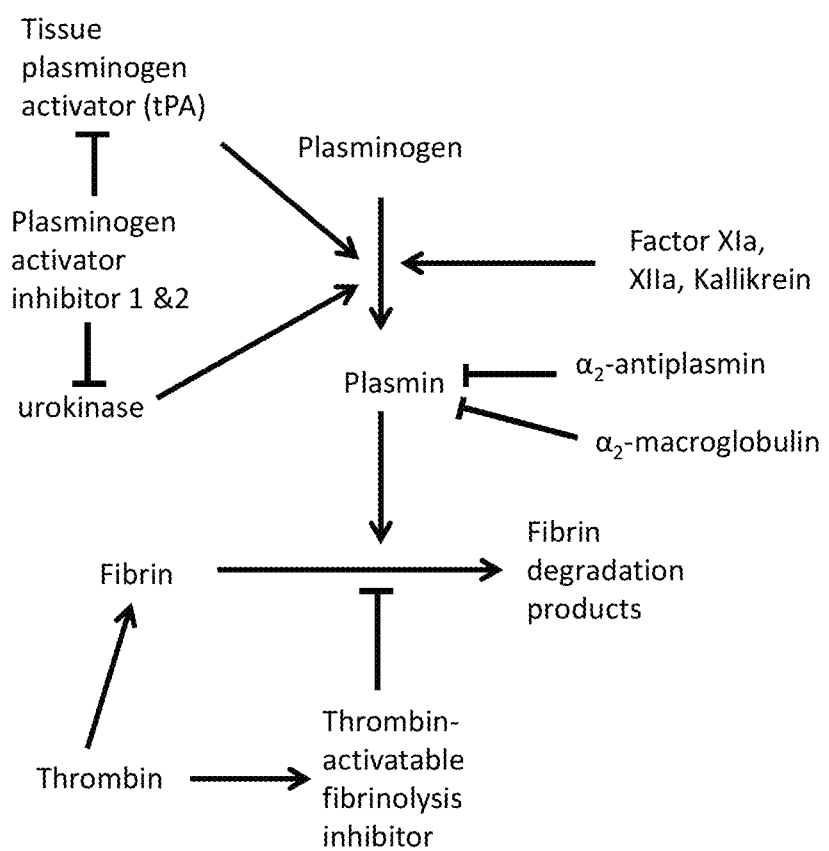
FIG. 2B is a schematic representation of fibrinolysis.

FIG. 2B presents another schematic representation of fibrinolysis which results in the creation of fibrin degradation products and thus clot dissolution. As indicated in the figure, plasminogen is activated to form plasmin, which can break down fibrin into fibrin degradation products. Tissue plasminogen activator (t-PA) and urokinase convert plasminogen to plasmin, thus allowing fibrinolysis to occur. t-PA and urokinase are themselves inhibited by plasminogen activator inhibitor-1 and plasminogen activator inhibitor-2 (PAI-1 and PAI-2). Alpha 2-antiplasmin and alpha 2-macroglobulin inactivate plasmin. Plasmin activity is also reduced by thrombin-activatable fibrinolysis inhibitor (TAFI), which modifies fibrin to make it more resistant to tPA-mediated plasminogen.

Example

Blood Clotting Time

Figure 3A:
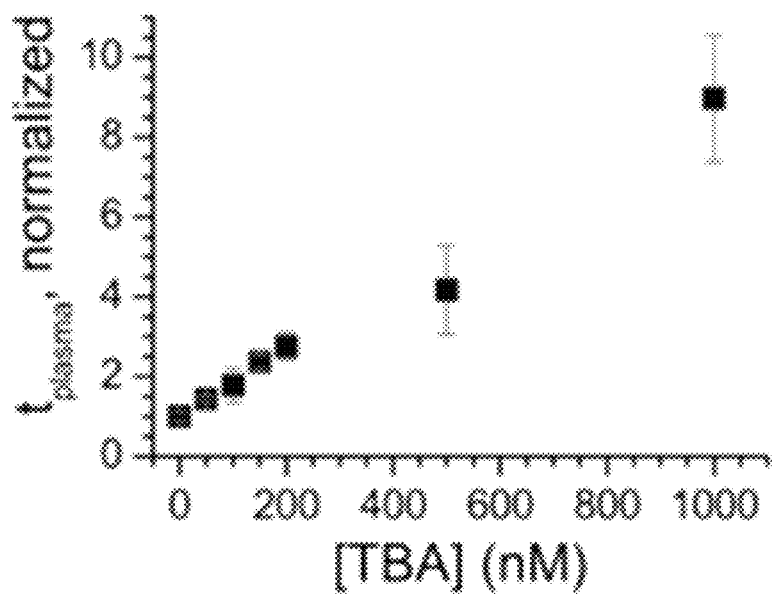
FIG. 3A is a graph of normalized blood clotting time ($t_{plasma}$) with increasing thrombin binding aptamer concentration.
Figure 3B:
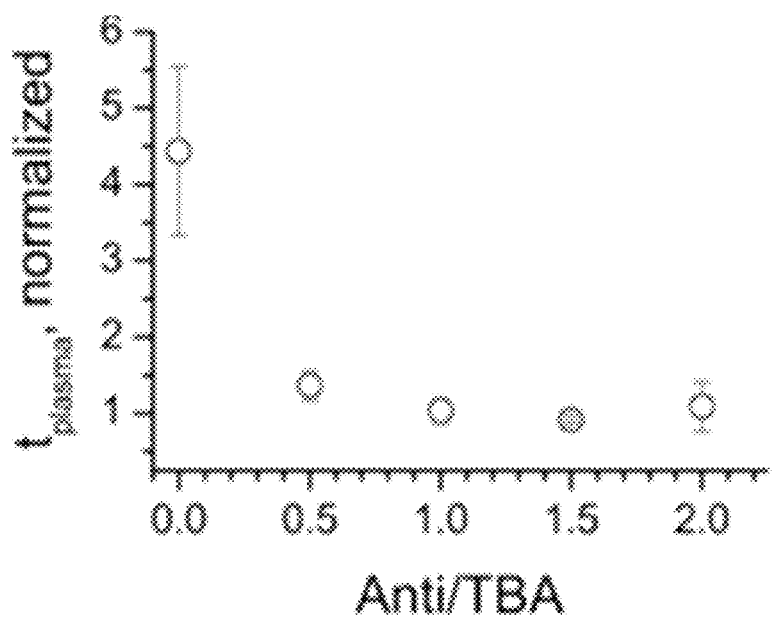
FIG. 3B is a graph of antidote introduced at a given concentration of aptamer to restore blood clotting time back to normal ($t_{plasma}=1.0$)

Without wishing to be bound by theory thrombin inhibition results in an increase in blood clotting time, $t_{plasma}$, as shown in a thrombin test measured by a coagulometer illustrated in FIGS. 3A and 3B. Blood with no TBA was normalized as $t_{plasma}=1.0$ in the depicted graphs. Increasing TBA concentration of TBA with the sequence 5'GGTTG-GTGTGGTTGG (SEQ ID NO: 1) increased $t_{plasma}$, see FIG. 3A, indicating that TBA inhibited thrombin and consequently blood coagulation. As illustrated in FIG. 1, complementary DNA can act as an antidote to TBA by base-pairing with it. This is confirmed in FIG. 3B where the addition of the DNA complement (sequence 5'AACCAACACAAC-CAA(SEQ ID NO: 2)) at ratios from 0:1 to 2:1 antidote:TBA caused $t_{plasma}$ to decrease to 1.0. Thus, the antidote can successfully inhibit TBA. Further, as confirmed by the blood clotting time being restored to its original value at 1:1 antidote:TBA, excess antidote is not needed to reverse TBA function. In view of the above, thrombin binding aptamer may be used to increase blood clotting time ($t_{plasma}$) with increasing concentration, demonstrating that TBA can be used to inhibit blood coagulation. Similarly, the noted antidote introduced to a given concentration of aptamer can restore blood clotting time back to normal (normalized $t_{plasma}=1.0$).

Example

Release Control Using Light

The wavelength of the surface plasmon resonance (SPR) maximum varies with nanorod shape and size allowing two nanorods to be chosen such that their SPRs do not overlap. In other words, gold nanorods can be synthesized with different sizes and shapes to have distinct absorption spectra that allow mutually exclusive excitation. Laser excitation at the SPR may be used to heat a nanoparticle, triggering release of a payload on the nanoparticle. In view of the above gold nanorods were synthesized using literature methods to have two different sizes and thus minimally overlapping SPRs for testing.

Figure 4A:
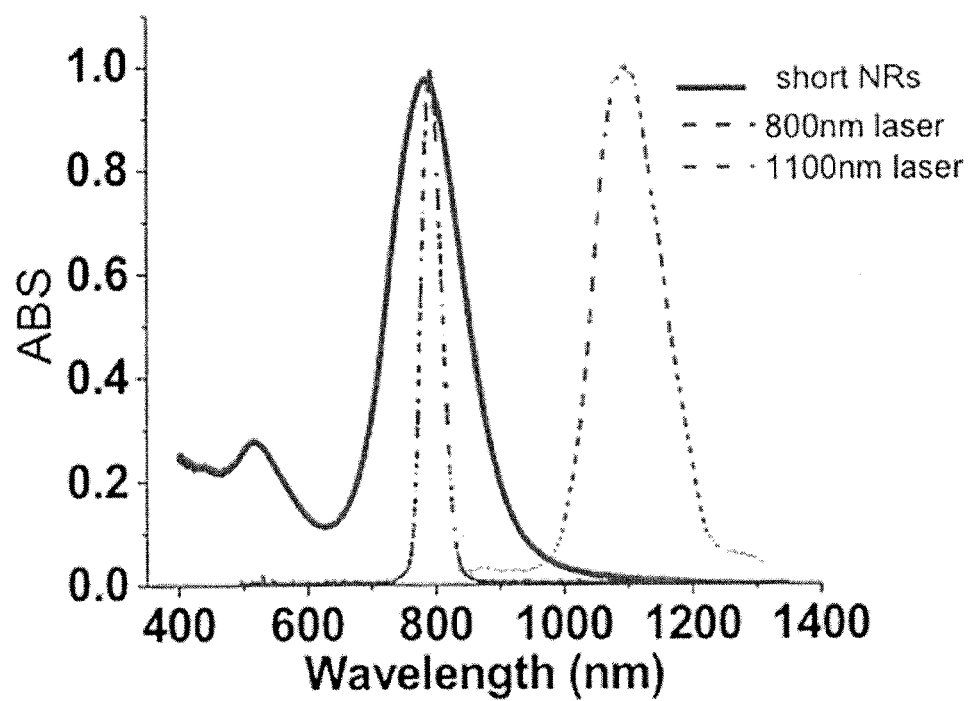
FIG. 4A is an absorption spectra of the short nanorods compared to 800 nm and 1100 nm lasers.
Figure 4B:
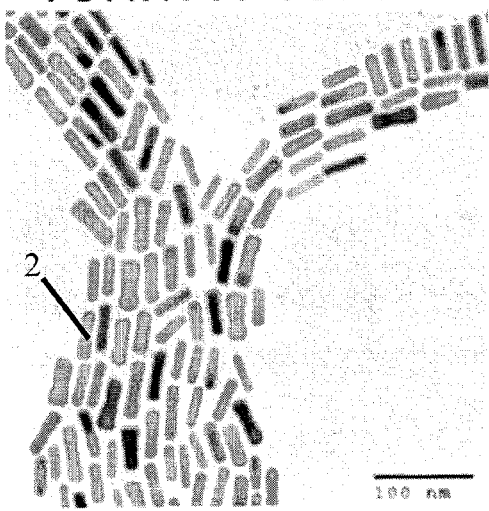
FIG. 4B is a micrograph of the short nanorods.
Figure 5A:
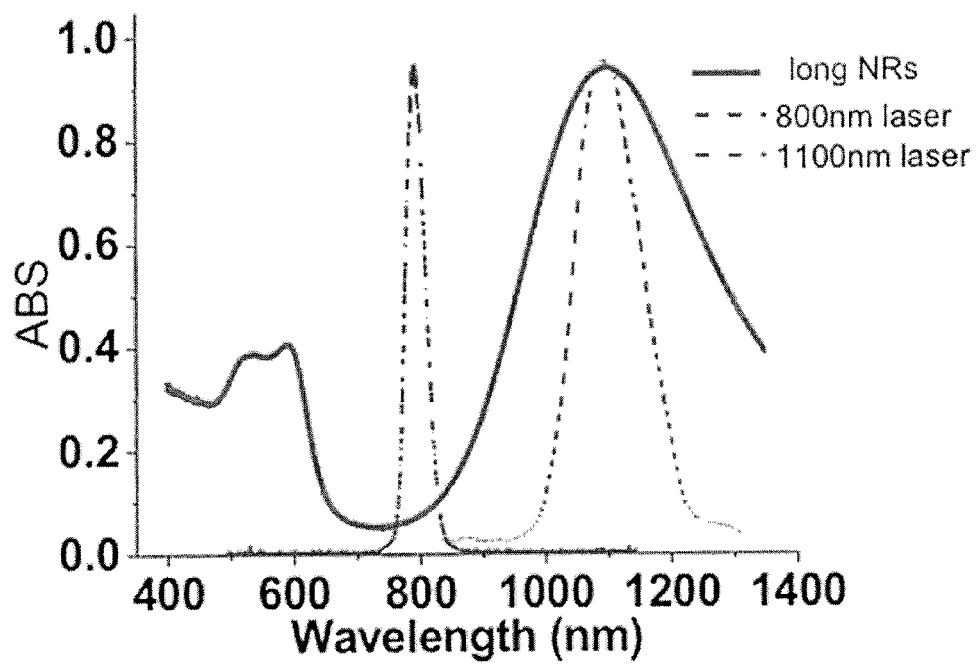
FIG. 5A is an absorption spectra of the long nanobones compared to 800 nm and 1100 nm lasers.
Figure 5B:
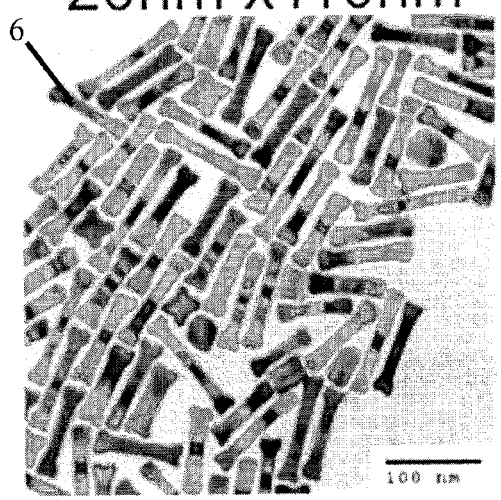
FIG. 5B is a micrograph of the long nanobones.

FIGS. 4A-5B illustrate the above concepts with images and absorption spectra of short nanorods (10 nm×40 nm) that absorb at 800 nm and long bone-shaped nanorods (20 nm×110 nm) that absorb at 1100 nm. As shown in FIG. 4A, the short nanorods absorb at 800 nm and overlap with an 800 nm laser but not an 1100 nm one. Similarly, FIG. 5A shows that the long bone-shaped nanorods absorb at 1100 nm and overlap with an 1100 nm laser but not an 800 nm one.

Example 4

Laser Irradiation of Loaded Nanoparticles

For testing purposes, TBA and the antidote were fluorescently labeled for quantification with different fluorophores (TBA with tetramethylrhodamine, TMR, λemission=580 nm, antidote with FAM, λemission=520 nm). The two different nanorods loaded with the TBA and antidote were mixed together, resulting in an absorption spectrum that had SPR peaks at both 800 nm and 1100 nm, see no irradiation curve in FIG. 6A.

Figure 6A:
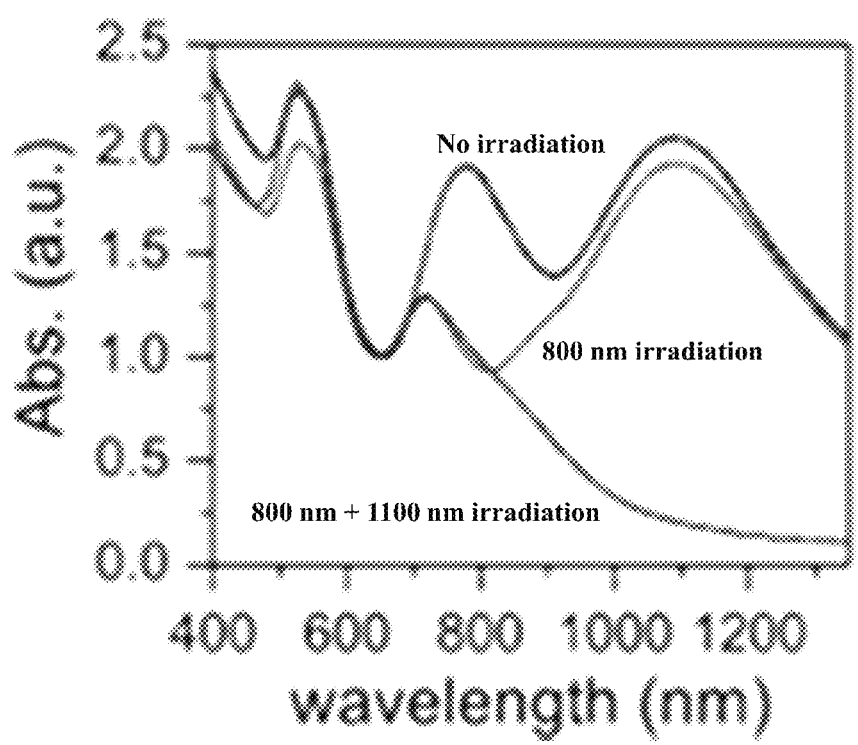
FIG. 6A is an absorption spectra of short nanorods loaded with a thrombin binding aptamer (TBA) and long nanorods loaded with antidote before irradiation, 800 nm irradiation, and 800 nm followed by 1100 nm irradiation.
Figure 6B:
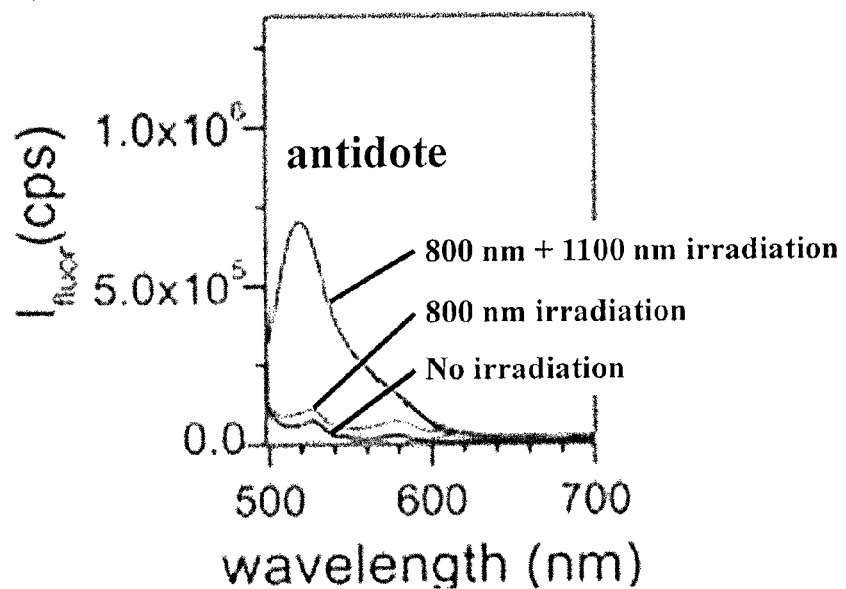
FIG. 6B is a graph of fluorescence of released supernatant, the antidote, before irradiation, after 800 nm irradiation, and after 800 nm irradiation followed by 1100 nm irradiation.
Figure 6C:
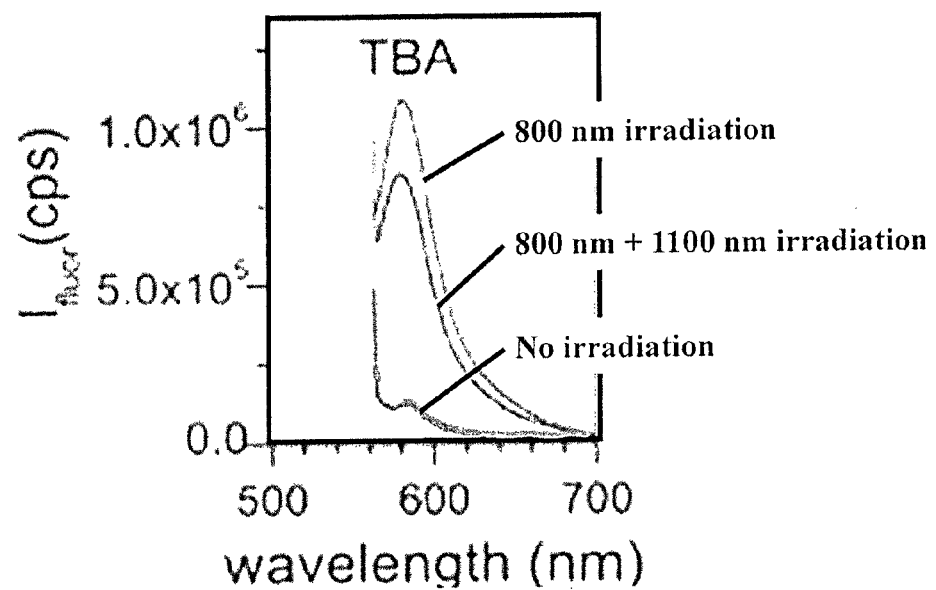
FIG. 6C is a graph of fluorescence of released supernatant, TBA, before irradiation, after 800 nm irradiation, and after 800 nm irradiation followed by 1100 nm irradiation.

FIGS. 6A-6C are an absorption spectra and graphs of fluorescence of released supernatant for short nanorods loaded with a thrombin binding aptamer (TBA) mixed with long nanorods loaded with antidote before irradiation, after 800 nm irradiation, and after 800 nm followed by 1100 nm irradiation. Specifically, laser irradiation at 800 nm was used to selectively excite the short nanorods and melt them, as evidenced by a decrease in the SPR at 800 nm, see 102 in FIG. 6A, while the peak at 1100 nm was not affected, showing that the long nanorods were unaffected. This released the thrombin binding aptamer, which was monitored by the increase in fluorescence at 580 nm due to its fluorescent tag. This resulted in an increase in $t_{plasma}$, see FIG. 6D, which is due to blood clotting being inhibited. To reverse the effect, laser excitation at 1100 nm melted the longer nanorods, as evidenced by the decrease in its SPR at 1100 nm, see FIG. 6A 800 nm and 1100 nm irradiation. This released the DNA antidote, as evidenced by the increase in fluorescence at 520 nm due to its fluorescent tag, see FIG. 6B. This resulted in a blood clotting time of $t_{plasma}$=0.88, see FIG. 6D. Thus, the antidote binds to the thrombin binding aptamer, so that it cannot inhibit thrombin and thus restored blood clotting.

Example 5

Comparison of Normalized Blood Clotting Times

Figure 6D:
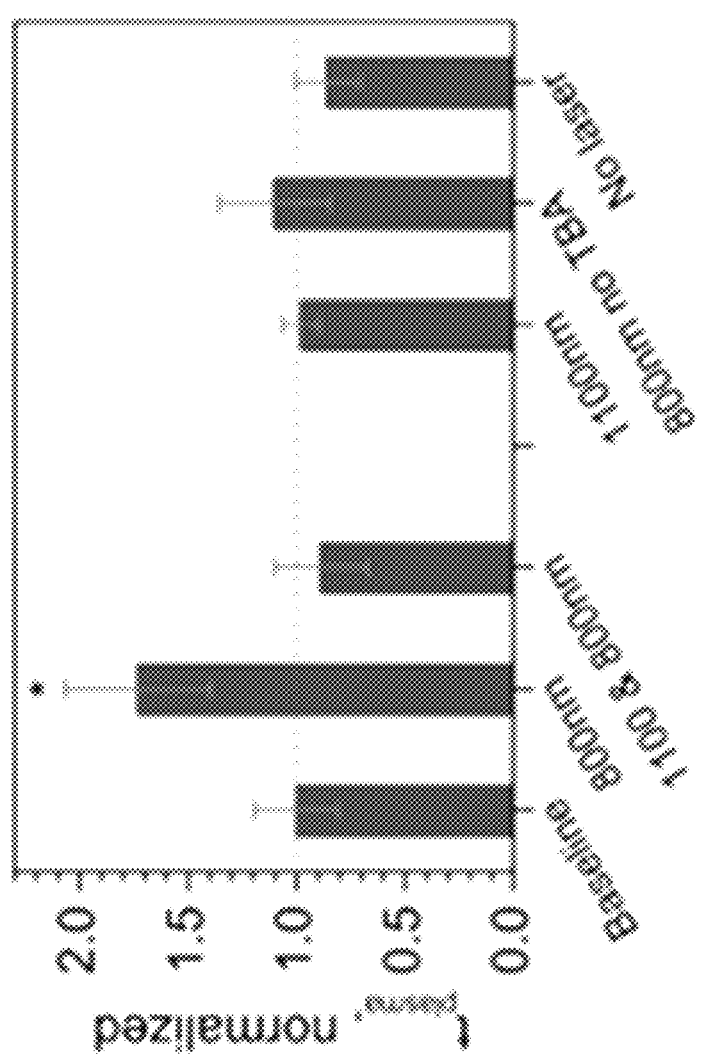
FIG. 6D is a graph comparing normalized blood clotting time ($t_{plasma}$) for different combinations of irradiation and materials.

FIG. 6D presents a graph comparing normalized $t_{plasma}$ for samples before irradiation (defined as 1.0) of a mixture of short nanorods loaded with TBA and long nanorods loaded with antidote to different testing conditions. 800 nm excitation increases $t_{plasma}$ to 1.73, and 800 nm+1100 nm excitation restores $t_{plasma}$ to 0.88. 1100 nm irradiation alone shows no increase in $t_{plasma}$. Irradiation at 800 nm of short nanorods without TBA and long nanorods with antidote shows no increase in $t_{plasma}$. To test the effect of the presence of the nanoparticles, a mixture not exposed to irradiation in blood shows no increase in $t_{plasma}$.

In addition to the above, 1100 nm irradiation alone did not significantly change $t_{plasma}$ (0.98, showing that antidote release alone does not affect coagulation. To test whether the protein corona release affects coagulation, nanorods with coronas were prepared without TBA and mixed with longer nanorods loaded with the antidote. 800 nm irradiation resulted in no significant change in $t_{plasma}$ (1.1), confirming that the presence of TBA was necessary to affect coagulation. Finally, it was verified that the presence of NR-HS-TBA+NB-HS-anti mixture with blood did not affect $t_{plasma}$ (0.86).

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A composition comprising:
 a nanoparticle with a first excitation wavelength; and
 a therapeutic agent selected from one of an anticoagulant and an anticoagulant antidote attached to the nanoparticle, wherein excitation of the nanoparticle with the first excitation wavelength releases the therapeutic agent.

2. The composition of claim 1, wherein the nanoparticle is at least one of a nanobone and a nanorod.

3. The composition of claim 1, wherein the nanoparticle is a gold nanoparticle.

4. The composition of claim 1, wherein the therapeutic agent is attached to the nanoparticle using at least one of adsorption and covalent bonding.

5. The composition of claim 1, wherein the therapeutic agent is released from the nanoparticle by melting the nanoparticle with the first excitation wavelength.

6. The composition of claim 1, wherein the therapeutic agent is the anticoagulant and the anticoagulant is a thrombin inhibitor.

7. The composition of claim 6, wherein the thrombin inhibitor is a DNA thrombin inhibitor.

8. The composition of claim 7, wherein the DNA thrombin inhibitor is a thrombin inhibiting aptamer.

9. The composition of claim 1, wherein the therapeutic agent is the anticoagulant antidote and the anticoagulant antidote is a DNA antidote of an anticoagulant.

10. The composition of claim 9, wherein the DNA antidote is a DNA antidote of a DNA thrombin inhibitor.

11. The composition of claim 1, wherein the first excitation wavelength comprises a wavelength to which tissue is transparent.

12. The composition of claim 1, further comprising a nanoparticle with a second excitation wavelength different from the first excitation wavelength, and wherein the therapeutic agent is the anticoagulant and the anticoagulant antidote is attached to the nanoparticle with the second excitation wavelength.

13. A method for controlling clotting, the method comprising:
 administering a first nanoparticle with a first excitation wavelength, wherein an anticoagulant is attached to the first nanoparticle;
 administering a second nanoparticle with a second excitation wavelength different from the first excitation wavelength, wherein an anticoagulant antidote is attached to the second nanoparticle;
 exciting the first nanoparticle with the first excitation wavelength to release the anticoagulant; and
 exciting the second nanoparticle with the second excitation wavelength to release the anticoagulant antidote.

14. The method of claim 13, wherein the first and second nanoparticles include at least one of a nanobone and a nanorod.

15. The method of claim 13, wherein the first and second nanoparticles are gold nanoparticles.

16. The method of claim 13, wherein the anticoagulant and anticoagulant antidote are attached to the first and second nanoparticles using at least one of a adsorption and covalent bonding.

17. The method of claim 13, wherein the anticoagulant is released from the first nanoparticle by melting the first nanoparticle with the first excitation wavelength.

18. The method of claim 17, wherein the anticoagulant antidote is released from the second nanoparticle by melting the second nanoparticle with the second excitation wavelength.

19. The method of claim 13, wherein the anticoagulant is a thrombin inhibitor.

20. The method of claim 19, wherein the thrombin inhibitor is a DNA thrombin inhibitor.

21. The method of claim 20, wherein the DNA thrombin inhibitor is a thrombin inhibiting aptamer.

22. The method of claim 13, wherein the anticoagulant antidote is a DNA antidote of a thrombin inhibitor.

23. The method of claim 13, wherein the first excitation wavelength comprises a wavelength to which tissue is transparent.

24. The method of claim 13, wherein exciting the first nanoparticle and/or second nanoparticle further comprises exciting the first nanoparticle and/or second nanoparticle with a laser.

* * * * *